United States Patent
Goto et al.

(10) Patent No.: US 7,354,938 B2
(45) Date of Patent: Apr. 8, 2008

(54) PYRAZOLE COMPOUNDS AND USES RELATED THERETO

(75) Inventors: Hiroyuki Goto, Takatsuki (JP); Makoto Kakutani, Takatsuki (JP); Jun Nishiu, Takatsuki (JP); Yasuhiro Ohe, Takatsuki (JP); Jay P. Powers, Pacifica, CA (US); Shinji Yata, Takatsuki (JP); Hua Tu, San Carlos, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 11/084,734

(22) Filed: Mar. 18, 2005

(65) Prior Publication Data

US 2005/0272793 A1     Dec. 8, 2005

Related U.S. Application Data

(60) Provisional application No. 60/556,013, filed on Mar. 23, 2004.

(51) Int. Cl.
*A61K 31/4439* (2006.01)
*C07D 401/04* (2006.01)

(52) U.S. Cl. .................... 514/341; 546/275.4

(58) Field of Classification Search ............. 546/275.4; 514/341

See application file for complete search history.

(56) References Cited

U.S. PATENT DOCUMENTS 6,248,755 B1     6/2001   Chapman et al.
2003/0045554 A1*  3/2003   Sankaranarayanan ....... 514/340

FOREIGN PATENT DOCUMENTS

WO   WO 03/104207 A2   12/2003
WO   WO 03/104208 A1   12/2003
WO   WO 2005/095350 A1  10/2005

OTHER PUBLICATIONS

Chang et al., Bioorganic and Medicinal Chemistry Letters, 11 (2001) 2549-2553.*
Bauer, et al., J. Med. Chem. (1968), 11(5), pp. 981-984.*
Chang et al., "Substituted Imidazoles as Glucagon Receptor Antagonists," *Bioorganic & Medicinal Chemistry Letters*, 11, 2001, pp. 2549-2553.

* cited by examiner

*Primary Examiner*—Rebecca Anderson
*Assistant Examiner*—Michael P. Barker
(74) *Attorney, Agent, or Firm*—Foley & Lardner LLP

(57) ABSTRACT

Substituted pyrazoles are provided that are useful for the treatment of, for example, diabetes, obesity and metabolic syndrome.

5 Claims, No Drawings

PYRAZOLE COMPOUNDS AND USES RELATED THERETO

CROSS-REFERENCES TO RELATED APPLICATIONS

This application claims the benefit of U.S. Provisional Application Ser. No. 60/556,013, filed Mar. 23, 2004, the content of which is incorporated herein by reference.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The present invention relates to pyrazole compounds having HSD1 inhibitory activity. 11-Beta-hydroxysteroid dehydrogenase 1 (hereinafter, "11β-HSD1" or "HSD1") catalyzes the interconversion of glucocorticoids (hereinafter, "GC") between inert 11-keto forms (e.g. cortisone, 11-dehydrocorticosterone) and active 11β-hydroxy forms (e.g. cortisol, corticosterone, respectively). The enzyme, in vivo, prefers the reductase direction from 11-keto to 11β-hydroxy, in other words, the production of active GC.

11β-HSD1 is ubiquitously expressed, most notably in liver, lung, adipose tissue, vasculature, ovary and the central nervous system.

Recently, experimental results have suggested that the active form of GC produced through HSD1 as well as the enzyme itself is involved in several biological actions and diseases.

For example, the active GC is known to stimulate gluconeogenic enzymes and have effects at least in part in inducing hyperglycemia. In this situation, HSD1 can be a second source of GC production in addition to the adrenal glands.

As another example, continuous excess of the active GC in peripheral tissues, as observed in Cushing's syndrome, leads to insulin resistance, where HSD1 is considered to have an important role.

Also, in adipose tissue, active GC has been demonstrated to enhance the differentiation of preadipocytes into adipocytes. Mature adipocytes express HSD1 activity, which causes an increase in local concentration of the active form and further expansion of adipose tissue. Such an action of HSD1 should be critical in pathogenesis of obesity.

In addition, a local immunosuppressive effect of HSD1 in placental deciduas, and a relationship between the expression of the enzyme in adrenal cortex and the induction of adrenaline synthesis, have been suggested.

(The above are referred to in: Quinkler M, Oelkers W & Diederich S (2001) European Journal of Endocrinology Vol. 144, Pages 87-97; and Seckl J R & Walker B R (2001) Endocrinology Vol. 142, Pages 1371-1376.)

According to the above suggestions, it is expected that drugs having inhibitory effects against HSD1 would be useful for treating or preventing diabetes mellitus, obesity, metabolic syndrome in connection with any of such diseases, or any other diseases which occur by reason of the actions of HSD1.

Diabetes mellitus, the main feature of which disease is chronic hyperglycemia, introduces various metabolic abnormalities and shows symptoms of thirst, polydipsia, polyuria, and so on based on high glucose concentration. A continuing hyperglycemic state can also lead to diabetic complications such as retinopathy, nephropathy, neuropathy, and myocardial and/or cerebral infarction by reason of arteriosclerosis.

In treating diabetes, moderate suppression of hyperglycemia is critical in order that onset and progress of the complications would be repressed. For these purposes, dietetics, ergotherapy and pharmacotherapy are utilized in combination on a suitable basis and, amongst the pharmacotherapy, many approaches different in mechanisms of action have been attempted. In spite of those various existing methods, sufficient therapeutic effect has not ever been achieved.

Obesity is defined as a state of fatness coinciding with any disease that would be improved or not be progressed in case of weight decrease (e.g. diabetes, hyperlipidemia, hypertension) or with an excessive amount of fat in viscera. It is considered that, if such a state should continue, at least two of diabetes, hyperlipidemia, hypertension and related disorders would concur, followed by the onset of myocardial and/or cerebral infarction by reason of arteriosclerosis.

Major therapeutic methods in treating obesity are dietetics and ergotherapy, and pharmacotherapy is undertaken only if necessary, for example, because of difficulty in the first two alternatives. However, the existing drugs have several problems in adverse effects and usages, since most of them suppress feeding mainly via central action.

In consequence, development of any drug to treat diabetes and/or obesity with a novel mechanism of action has so far been required. Under these circumstances, it is expected that drugs having inhibitory effects against HSD1 would be useful as another alternative with separate mechanistic approach to treat diabetes mellitus, as well as a novel "adipose tissue-acting" class among other drugs against obesity.

As drugs in development to treat diabetes and/or obesity through inhibition of HSD1, for example, WO 03/104207 and WO 03/104208 disclose triazole compounds of the following general formula:

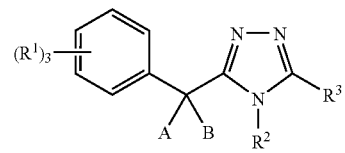

wherein:

A and B are taken separately or together;

when taken separately, A is halo, unsubstituted or substituted $C_{1-6}$alkyl, unsubstituted or substituted $OC_{1-6}$alkyl or unsubstituted or substituted phenyl and B is —H, halo, unsubstituted or substituted $C_{1-6}$alkyl, unsubstituted or substituted $OC_{1-6}$alkyl, unsubstituted or substituted —$SC_{1-6}$alkyl, unsubstituted or substituted $C_{2-6}$alkenyl, unsubstituted or substituted phenyl or unsubstituted or substituted naphthyl; and when taken together, unsubstituted or substituted $C_{1-4}$alkylene or unsubstituted or substituted $C_{2-5}$alkanediyl;

each $R^1$ is —H, —OH, halo, unsubstituted or substituted $C_{1-10}$alkyl, unsubstituted or substituted $C_{1-6}$alkoxy or unsubstituted or substituted $C_{6-10}$aryl, or two $R^1$ taken together are a fused $C_{5-6}$alkyl (either unsubstituted or substituted) or unsubstituted or substituted aryl ring;

$R^2$ and $R^3$ are taken separately or together;

when taken together, (a) a $C_{3-8}$ alkanediyl forming a fused 5-10 membered non-aromatic ring (optionally interrupted with 1-2 double bonds, either unsubstituted or substituted) or (b) a fused 6-10 membered aromatic monocyclic (either unsubstituted or substituted) or bicyclic group (either unsubstituted or substituted);

when taken separately, $R^2$ is $C_{1-14}$ alkyl (either unsubstituted or substituted), unsubstituted or substituted phenyl, unsubstituted or substituted pyridyl, either unsubstituted or substituted $C_{2-10}$ alkenyl, —$CH_2CO_2H$, —$CH_2CO_2C_{1-6}$ alkyl, —$CH_2C(O)NHR^a$, —$NHR^a$ or $N(R^a)_2$ and $R^3$ is unsubstituted or substituted $C_{1-4}$alkyl, unsubstituted or substituted $C_{2-10}$alkenyl, unsubstituted or substituted $SC_{1-6}$ alkyl, unsubstituted or substituted $C_{6-10}$aryl, unsubstituted or substituted heterocyclyl or unsubstituted or substituted heteroaryl;

$R^a$ is unsubstituted or substituted $C_{1-3}$ alkyl, unsubstituted or substituted $OC_{1-3}$ alkyl, unsubstituted or substituted $C_{6-10}$ $ArC_{1-6}$alkylene or unsubstituted or substituted phenyl;

However, the description provided in the noted applications does not disclose or suggest any of the compounds having the structure of the present invention.

The compounds of the present invention improve physicochemical (stability, etc.) and biological (activity to inhibit HSD1, specificity, bioavailability, metabolism, etc.) profiles, as a result of the selection of structural characteristics as disclosed herein.

BRIEF SUMMARY OF THE INVENTION

According to the present invention, it has been found that pyrazole compounds represented by the following formula have superior HSD1 inhibitory activity, and are useful as HSD1 inhibitors or therapeutic drugs for the treatment of diabetes or obesity.

The present invention provides the following:

In one aspect, the present invention provides pyrazole compounds represented by the following formula:

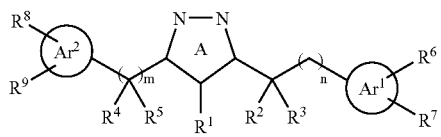

wherein
$R^1$ is a hydrogen atom, —CO—O-alkyl, —COOH, an alkyl group, an alkoxy group or a cycloalkyl group, wherein the alkyl group, the alkoxy group and the cycloalkyl group are optionally substituted by 1 to 5 substituents each independently selected from a halogen atom, a haloalkyl group, —OH, —$NH_2$, an alkoxy group, a cycloalkyl group, an alkenyl group, —COOH, —CO—O-alkyl, —CO—$N(R^{10})$ $(R^{11})$, —$N(R^{10})$—CO—$R^{11}$, an aryl group and a heteroaryl group, wherein $R^{10}$ and $R^{11}$ are each independently a hydrogen atom or an alkyl group, and the aryl group and the heteroaryl group are optionally substituted by 1 to 3 substituents each independently selected from a halogen atom, a haloalkyl group, an alkyl group, —$(CH_2)_h$—OH, —$N(R^{12})(R^{13})$, —CN, —$NO_2$, an alkoxy group, a cycloalkyl group, an alkenyl group, —CO—$R^{14}$, an aryl group and a heteroaryl group, wherein h is 0-3, $R^{12}$ and $R^{13}$ are each independently a hydrogen atom, an alkyl group or —CO-alkyl, and $R^{14}$ is —OH, an alkoxy group, an alkyl group or —$N(R^{15})(R^{16})$, wherein $R^{15}$ and $R^{16}$ are each independently a hydrogen atom or an alkyl group;

$R^2$, $R^3$, $R^4$ and $R^5$ are each independently a hydrogen atom, an alkyl group, an alkoxy group, a cycloalkyl group or $R^2$ and $R^3$, and/or $R^4$ and $R^5$ in combination with the carbon atoms to which they are attached form a ring represented by

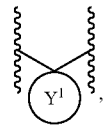

wherein the $Y^1$ ring is a cycloalkane or a heterocycloalkane group, the wavy lines indicate the point of attachment to the remainder of the molecule and wherein the cycloalkane group and the heterocycloalkane group are optionally substituted by 1 to 3 substituents each independently selected from a halogen atom, a haloalkyl group, an alkyl group, —$(CH_2)_h$—OH, —$N(R^{12})(R^{13})$, —CN, —$NO_2$, an alkoxy group, a cycloalkyl group, an alkenyl group, —CO—$R^{14}$, an aryl group and a heteroaryl group (h, $R^{12}$, $R^{13}$ and $R^{14}$ are as defined above), wherein the alkyl group, the alkoxy group and the cycloalkyl group are optionally substituted by 1 to 5 substituents each independently selected from a halogen atom, a haloalkyl group, —OH, —$NH_2$, an alkoxy group, a cycloalkyl group, an alkenyl group, —COOH, —CO—O-alkyl, —CO—$N(R^{10})(R^{11})$, an aryl group and a heteroaryl group wherein the aryl group and the heteroaryl group are optionally substituted by 1 to 3 substituents each independently selected from a halogen atom, a haloalkyl group, an alkyl group, —$(CH_2)_h$—OH, —$N(R^{12})(R^{13})$, —CN, —$NO_2$, an alkoxy group, a cycloalkyl group, an alkenyl group, —CO—$R^{14}$, an aryl group and a heteroaryl group ($R^{10}$, $R^{11}$, h, $R^{12}$, $R^{13}$ and $R^{14}$ are as defined above);

the subscript n is an integer of from 0 to 3;

$Ar^1$ is an aryl group or a heteroaryl group;

$R^6$ and $R^7$ are each independently a hydrogen atom, a halogen atom, a haloalkyl group, an alkyl group, —$(CH_2)_j$—OH, —$N(R^{12})(R^{13})$, —CN, —$NO_2$, an alkoxy group, a cycloalkyl group, an alkenyl group, —CO—$R^{14}$, an aryl group or heteroaryl group, wherein j is 0-3, and the aryl group and the heteroaryl group are optionally substituted by 1 to 3 substituents each independently selected from a halogen atom, a haloalkyl group, an alkyl group, —$(CH_2)_h$—OH, —$N(R^{12})(R^{13})$, —CN, —$NO_2$, an alkoxy group, a cycloalkyl group, an alkenyl group, —CO—$R^{14}$, an aryl group and a heteroaryl group ($R^{12}$, $R^{13}$, $R^{14}$ and h are as defined above);

the subscript m is an integer of from 0 to 3;

$R^8$ and $R^9$ are each independently a hydrogen atom, a halogen atom, —OH, —$NO_2$, —CN, an alkyl group, an alkoxy group, —CO—$R^{17}$, —$SO_2$—$R^{17}$, —CO—$N(R^{18})$ $(R^{19})$, —$N(R^{20})(R^{21})$ or in combination form —O-alkylene-O—, wherein the alkyl group and the alkoxy group are optionally substituted by 1 to 5 substituents each independently selected from a halogen atom, a haloalkyl group, —OH, —$NH_2$, an alkoxy group, a cycloalkyl group, an alkenyl group, —COOH, —CO—O-alkyl, —CO—N($R^{10}$)($R^{11}$), —N($R^{10}$)—CO—$R^{11}$, an aryl group and a heteroaryl group, wherein the aryl group and the heteroaryl group are optionally substituted by 1 to 3 substituents each independently selected from a halogen atom, a haloalkyl group, an alkyl group, —$(CH_2)_h$—OH, —N($R^{12}$)($R^{13}$), —CN, —$NO_2$, an alkoxy group, a cycloalkyl group, an alkenyl group, —CO—$R^{14}$, an aryl group and a heteroaryl group ($R^{10}$, $R^{11}$, h, $R^{12}$, $R^{13}$ and $R^{15}$ are as defined above), $R^{17}$ is —OH, an alkoxy group, an alkyl group, —$NH_2$, —NH-alkyl or —N(-alkyl)$_2$, wherein the alkoxy group and alkyl groups are optionally substituted by substituents each independently selected from —OH, —$SO_2$—$R^{22}$ and —$(CH_2)_t$—CO—$R^{23}$, wherein t is 0-3, $R^{22}$ is an alkyl group or —$NH_2$, and $R^{23}$ is an alkyl group, —NH-alkyl, —N(-alkyl)$_2$, or —$NH_2$, wherein the alkyl groups are optionally substituted by substituents each independently selected from —OH, an alkoxy group or —$(CH_2)_u$—N($R^{24}$)($R^{25}$), wherein u is 0-3, and $R^{24}$ and $R^{15}$ are each independently a hydrogen atom, an alkyl group or —CO-alkyl, $R^{18}$ and $R^{19}$ are each independently a hydrogen atom, an alkyl group or —$(CH_2)_p$—$R^{26}$, wherein p is 0-3 and $R^{26}$ is —OH, a haloalkyl group, an alkoxy group, —CO—$NH_2$ or —N($R^{24}$)($R^{25}$), wherein $R^{24}$ and $R^{25}$ are as defined above;

$R^{20}$ and $R^{21}$ are each independently a hydrogen atom, an alkyl group —CO—$R^{23}$ or in combination with the nitrogen atom to which each is attached, form

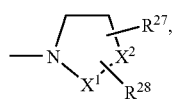

wherein the alkyl group is optionally substituted by substituents each independently selected from —OH, —$SO^2$—$R^{22}$ and —$(CH_2)_t$—CO—$R^{23}$ (wherein $R^{22}$ and $R^{23}$ are as defined above, $X^1$ is —CO—, —$CH_2$— or —$CH_2$—$CH_2$—, $X^2$ is —O—, —$(CH_2)_q$— or —N($R^{29}$)— or a spirocyclic ring represented by

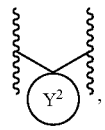

wherein q is 0-2, $R^{29}$ is a hydrogen atom, —CO—$R^{30}$, —$SO_2$—$R^{30}$ or —$(CH_2)_r$—$Ar^3$, wherein $R^{30}$ is an alkyl group, an alkoxy group, —NH-alkyl or —N(-alkyl)$_2$, r is 0-3, and $Ar^3$ is an aryl group or heteroaryl group, wherein the aryl group and heteroaryl group are optionally substituted by 1 to 3 substituents each independently selected from a halogen atom, a haloalkyl group, an alkyl group, —$(CH_2)_h$—OH, —N($R^{12}$)($R^{13}$), —CN, —$NO_2$, an alkoxy group, a cycloalkyl group, an alkenyl group, —CO—$R^{14}$, an aryl group and a heteroaryl group (h, $R^{12}$, $R^{13}$ and $R^{14}$ are as defined above), and the spirocyclic $Y^2$ ring is a spiro-cycloalkyl or spiro-heterocycloalkyl ring, and $R^{27}$ and $R^{28}$ are each independently a hydrogen atom, a halogen atom, a haloalkyl group, an alkyl group, —$(CH_2)_h$—OH, —N($R^{12}$)($R^{13}$), —CN, —$NO_2$, an alkoxy group, a cycloalkyl group, an alkenyl group, —CO—$R^{14}$, an aryl group or a heteroaryl group (h, $R^{12}$, $R^{13}$ and $R^{14}$ are as defined above);

$Ar^2$ is an aryl group, a heteroaryl group or a ring having the formula

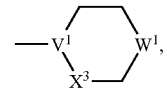

wherein $V^1$ is CH or N, $X^3$ is —$(CH_2)_v$—, wherein v is 0-2, and $W^1$ is —C($R^{31}$)($R^{32}$)—, —CO— or —N($R^{33}$)—, wherein $R^{31}$ and $R^{32}$ are each independently a hydrogen atom, an alkyl group, an alkoxy group, a haloalkyl group, —$(CH_2)_w$—OH, —CO—$R^{34}$, -$L^1$—$Ar^4$ or —N($R^{35}$)($R^{36}$), wherein w is 0-3, $R^{34}$ is —OH, an alkoxy group, an alkyl group or —N($R^{37}$)($R^{38}$), wherein $R^{37}$ and $R^{38}$ are each independently a hydrogen atom, an alkyl group, —$(CH_2)_x$—OH or an alkoxy group, wherein x is 0-3, $L^1$ is —$(CH_2)_y$—, —O— or —CO—, wherein y is 0-3, $Ar^4$ is an aryl group or a heteroaryl group, wherein the aryl group and the heteroaryl group are optionally substituted by 1 to 3 substituents each independently selected from a halogen atom, a haloalkyl group, an alkyl group, —$(CH_2)_h$—OH, —N($R^{12}$)($R^{13}$), —CN, —$NO_2$, an alkoxy group, a cycloalkyl group, an alkenyl group, —CO—$R^{14}$, an aryl group and a heteroaryl group (h, $R^{12}$, $R^{13}$ and $R^{14}$ are as defined above), and $R^{35}$ and $R^{36}$ are each independently a hydrogen atom, an alkyl group, —CO-alkyl, —CO—O-alkyl or $L^1$—$Ar^4$ ($L^1$ and $Ar^4$ are as defined above), and $R^{33}$ is a hydrogen atom, —CO—$R^{28}$, —$SO_2$—$R^{28}$ or —$(CH_2)_k$—$Ar^3$, wherein k is 0-3 ($R^{28}$ and $Ar^3$ are as defined above; and the pyrazole ring (labeled A) provided as

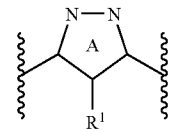

is selected from

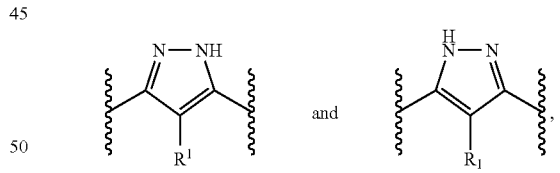

or a prodrug thereof or a pharmaceutically acceptable salt thereof.

In the above compounds of the invention, any variable used to define another variable is meant to have its most complete meaning as provided above, unless otherwise stated. Additionally, when a letter subscript is provided with a range (e.g., x and y being 0 to 3), the lower limit (0) is meant to indicate the presence of a bond.

In some embodiments, the pyrazole compound has the formula above, wherein the subscript m is 0, a prodrug thereof or a pharmaceutically acceptable salt thereof.

In other embodiments, the pyrazole compound has the formula above, wherein the subscript m is 0, and where $R^2$ and $R^3$ are in combination with the carbon atom to which they are attached to form

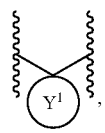

wherein the $Y^1$ ring is a $C_{3-8}$ cycloalkane group, and the compounds further include a prodrug thereof or a pharmaceutically acceptable salt thereof. Within this group of embodiments, preferably $Ar^1$ is an phenyl group. Still further preferred are those embodiments in which $R^6$ and $R^7$ are each independently a halogen atom or a hydrogen atom.

In another aspect, the present invention provides a pharmaceutical composition comprising one or more of the pyrazole compounds described above, a prodrug thereof or a pharmaceutically acceptable salt thereof, and a pharmaceutically acceptable carrier.

In yet another aspect, the present invention provides a HSD1 (11β-hydroxysteroid dehydrogenase 1) inhibitor comprising a pyrazole compound as described above, a prodrug thereof or a pharmaceutically acceptable salt thereof as an effective component.

In a related aspect, the present invention provides a therapeutic or prophylactic drug for diabetes, which comprises a pyrazole compound as described above, a prodrug thereof or a pharmaceutically acceptable salt thereof as an effective component.

In another aspect, the present invention provides a therapeutic or prophylactic drug for obesity, which comprises a pyrazole compound as described above, a prodrug thereof or a pharmaceutically acceptable salt thereof as an effective component.

In yet another aspect, the present invention provides a therapeutic or prophylactic drug for metabolic syndrome, which comprises a pyrazole compound as described above, a prodrug thereof or a pharmaceutically acceptable salt thereof as an effective component.

In still another aspect, the present invention provides a method for the treatment or prophylaxis of diabetes, which comprises administering an effective amount of a pyrazole compound described above, a prodrug thereof or a pharmaceutically acceptable salt thereof to a mammal.

In another aspect, the present invention provides a method for the treatment or prophylaxis of obesity, which comprises administering an effective amount of a pyrazole compound described above, a prodrug thereof or a pharmaceutically acceptable salt thereof to a mammal.

In yet another aspect, the present invention provides a method for the treatment or prophylaxis of metabolic syndrome, which comprises administering an effective amount of a pyrazole compound described above, a prodrug thereof or a pharmaceutically acceptable salt thereof to a mammal.

In still another aspect related to those above, methods are provided wherein a therapeutic regimen comprises the use of a pyrazole compound as described above, in combination with a different therapeutic drug for the treatment of diabetes. Preferably, the different therapeutic drug for diabetes is one or more pharmaceutical agents selected from the group consisting of an insulin preparation, a sulfonylurea, an insulin secretagogue, a sulfonamide, a biguanide, an α-glucosidase inhibitor, a PTP1B inhibitor and an insulin sensitizer. In other preferred embodiments, the different therapeutic drug for diabetes is one or more pharmaceutical agents selected from the group consisting of insulin, glibenclamide, tolbutamide, glyclopyramide, acetohexamide, glimepiride, tolazamide, gliclazide, nateglinide, glybuzole, metformin hydrochloride, buformine hydrochloride, voglibose, acarbose and pioglitazone hydrochloride.

In another aspect related to those above, methods are provided wherein a therapeutic regimen comprises the use of a pyrazole compound as described above for obesity, which is used in combination with a different therapeutic drug for the treatment of diabetes. Preferably, the different therapeutic drug for diabetes is one or more pharmaceutical agents selected from the group consisting of an insulin preparation, a sulfonylurea, an insulin secretagogue, a sulfonamide, a biguanide, an α-glucosidase inhibitor, a PTP1B inhibitor and an insulin sensitizer. In other preferred embodiments, the different therapeutic drug for diabetes is one or more pharmaceutical agents selected from the group consisting of insulin, glibenclamide, tolbutamide, glyclopyramide, acetohexamide, glimepiride, tolazamide, gliclazide, nateglinide, glybuzole, metformin hydrochloride, buformine hydrochloride, voglibose, acarbose and pioglitazone hydrochloride.

In yet another aspect related to those above, methods are provided wherein a therapeutic regimen comprises the use of a pyrazole compound as described above for metabolic syndrome, which is used in combination with a different therapeutic drug for the treatment of diabetes. Preferably, the different therapeutic drug for diabetes is one or more pharmaceutical agents selected from the group consisting of an insulin preparation, a sulfonylurea, an insulin secretagogue, a sulfonamide, a biguanide, an α-glucosidase inhibitor, a PTP1B inhibitor and an insulin sensitizer. In other preferred embodiments, the different therapeutic drug for diabetes is one or more pharmaceutical agents selected from the group consisting of insulin, glibenclamide, tolbutamide, glyclopyramide, acetohexamide, glimepiride, tolazamide, gliclazide, nateglinide, glybuzole, metformin hydrochloride, buformine hydrochloride, voglibose, acarbose and pioglitazone hydrochloride.

In still another aspect related to those above, methods are provided wherein a therapeutic regimen comprises the use of a pyrazole compound as described above for diabetes, which is used in combination with a different therapeutic drug for the treatment of obesity. Preferably, the different therapeutic drug for obesity is Mazindol.

In another aspect related to those above, methods are provided wherein a therapeutic regimen comprises the use of a pyrazole compound as described above for obesity, which is used in combination with a different therapeutic drug for the treatment of obesity. Preferably, the different therapeutic drug for obesity is Mazindol.

In yet another aspect related to those above, methods are provided wherein a therapeutic regimen comprises the use of a pyrazole compound as described above for metabolic syndrome, which is used in combination with a different therapeutic drug for the treatment of obesity. Preferably, the different therapeutic drug for obesity is Mazindol.

BRIEF DESCRIPTION OF THE DRAWINGS

Not applicable.

DETAILED DESCRIPTION OF THE INVENTION

Compounds of the present invention have been described above. More specifically, respective substituents and moieties used in the present specification are defined in the following.

The "alkyl group" means a straight chain or branched chain alkyl group. Examples thereof include methyl group, ethyl group, propyl group, isopropyl group, butyl group, isobutyl group, sec-butyl group, tert-butyl group, pentyl group, isopentyl group, neopentyl group, tert-pentyl group, 1-ethylpropyl group, hexyl group and the like. It is preferably a straight chain or branched chain alkyl group having 1 to 6, more preferably 1 to 4, carbon atoms.

For $R^1$, $R^2$, $R^3$, $R^4$, $R^5$, $R^6$, $R^7$, $R^8$, R9, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, and $R^{38}$, preferred are methyl, ethyl, propyl, isopropyl, butyl and isobutyl, and particularly preferred are methyl and isopropyl.

The "cycloalkyl group" means a saturated cyclic alkyl group. Examples thereof include cyclopropyl group, cyclobutyl group, cyclopentyl group, cyclohexyl group, cycloheptyl group, cyclooctyl group and the like. It is preferably a cycloalkyl group having 3 to 8, more preferably 3 to 6, carbon atoms.

For $R^1$, $R^2$, $R^3$, $R^4$, $R^5$, $R^6$, $R^7$, $R^{27}$, $R^{28}$, $Y^1$ and $Y^2$, preferred are cyclopropyl, cyclobutyl and cyclopentyl, and particularly preferred is cyclopropyl. In the case of $Y^1$ and $Y^2$, the rings are attached in a spirocyclic manner to the remainder of the molecule.

The "heterocycloalkyl group" means a saturated 5- to 7-membered heterocyclic group containing 1 to 3 heteroatoms selected from the group consisting of nitrogen atom, oxygen atom and sulfur atom. Examples thereof include tetrahydrofuryl group, tetrahydrothienyl group, pyrrolidinyl group, pyrazolidinyl group, imidazolidinyl group, oxazolidinyl group, thiazolidinyl group, tetrahydropyranyl group, dioxolanyl group, dioxanyl group, piperidinyl group, piperazinyl group, morpholinyl group and the like.

For $Y^1$ and $Y^2$, preferred is piperidinyl, which in the case of the $Y^2$ ring is attached in a spirocyclic manner to the remainder of the molecule.

The "alkenyl group" means a straight chain or branched chain alkenyl group. Examples thereof include vinyl group, 1-propenyl group, allyl group, 1-methyl-2-propenyl group, 1-butenyl group, 2-butenyl group, 3-butenyl group, 1-pentenyl group, 2-pentenyl group, 1-hexenyl group, 2-hexenyl group and the like. It is preferably a straight chain or branched chain alkenyl group having 2 to 6, more preferably 2 to 4, carbon atoms.

For $R^6$, $R^7$, $R^{27}$ and $R^{28}$, preferred is vinyl.

The "aryl group" means an aromatic hydrocarbon group. Examples thereof include phenyl group, naphthyl group, anthryl group and the like. It is preferably a phenyl group or naphthyl group.

For $R^6$, $R^7$, $R^{27}$, $R^{28}$, $Ar^1$, $Ar^2$, $Ar^3$ and $Ar^4$, preferred are phenyl and naphthyl, and particularly preferred is phenyl.

The "heteroaryl group" means a monocyclic or fused 5- to 14-membered aromatic heterocyclic group containing 1 to 3 heteroatoms selected from the group consisting of nitrogen atom, oxygen atom and sulfur atom. Examples thereof include furyl group, thienyl group, pyrrolyl group, oxazolyl group, isooxazolyl group, thiazolyl group, isothiazolyl group, imidazolyl group, pyrazolyl group, pyridyl group, pyridazinyl group, pyrimidinyl group, pyrazinyl group, indolyl group, isoindolyl group, benzofuranyl group, benzothienyl group, benzoimidazolyl group, benzoxazolyl group, indolizinyl group, quinolyl group, isoquinolyl group, quinazolinyl group, cinnolinyl group, quinoxalinyl group, phthalazinyl group, acridinyl group, phenazinyl group, naphthyridinyl group and the like. It is preferably a monocyclic or fused 5- to 10-membered aromatic heterocyclic group containing 1 to 3 heteroatoms selected from the group consisting of nitrogen atom, oxygen atom and sulfur atom, which includes furyl group, thienyl group, pyrrolyl group, oxazolyl group, isooxazolyl group, thiazolyl group, isothiazolyl group, imidazolyl group, pyrazolyl group, pyridyl group, pyridazinyl group, pyrimidinyl group, pyrazinyl group, indolyl group, isoindolyl group, benzofuranyl group, benzothienyl group, benzoimidazolyl group, benzothiazolyl group, benzooxazolyl group and the like.

For $R^6$, $R^7$, $Ar^1$, preferred are thienyl, pyrrolyl and pyridyl.

For $R^{27}$, $R^{28}$, $Ar^2$, preferred are thienyl, pyrrolyl, oxazolyl, isooxazolyl, thiazolyl, imidazolyl, pyrazolyl and pyridyl, and particularly preferred are thienyl and pyridyl.

For $Ar^3$ and $Ar^4$, preferred is pyridyl.

The "halogen atom" means fluorine atom, chlorine atom, bromine atom or iodine atom. It is preferably fluorine atom or chlorine atom.

For $R^6$ and $R^7$, preferred is fluorine atom or chlorine atom. In this case, $Ar^1$ is particularly preferably phenyl, where only the 4-position of the phenyl is substituted by fluorine atom or chlorine atom.

For $R^8$ and $R^9$, preferred is chlorine atom. In this case, $Ar^2$ is particularly preferably phenyl, where at least the 2-position of the phenyl is substituted by chlorine atom.

For $R^{27}$ and $R^{28}$, preferred are fluorine atom or chlorine atom.

The "haloalkyl group" means a haloalkyl group wherein the above-defined "alkyl group" is substituted by the above-defined "halogen atom". Examples thereof include fluoromethyl group, difluoromethyl group, trifluoromethyl group, bromomethyl group, chloromethyl group, 1,2-dichloroethyl group, 2,2-dichloroethyl group, 2,2,2-trifluoroethyl group and the like. It is preferably a straight chain or branched chain haloalkyl group having 1 to 6, more preferably 1 to 4, carbon atoms, particularly preferably a trifluoromethyl group.

For $R^6$, $R^7$, $R^{26}$, $R^{27}$, $R^{28}$, $R^{31}$ and $R^{32}$, preferred are fluoromethyl group, difluoromethyl group or trifluoromethyl group.

The "alkoxy group" means a straight chain or branched chain alkoxy group. Examples thereof include methoxy group, ethoxy group, propoxy group, isopropoxy group, butoxy group, isobutoxy group, tert-butoxy group, pentyloxy group, hexyloxy group and the like. It is preferably a straight chain or branched chain alkoxy group having 1 to 6, more preferably 1 to 4, carbon atoms.

For $R^1$, $R^2$, $R^3$, $R^4$, $R^5$, $R^6$, $R^7$, $R^8$, $R^9$, $R^{14}$, $R^{17}$, $R^{26}$, $R^{27}$, $R^{28}$, $R^{30}$, $R^{31}$, $R^{32}$, $R^{34}$, $R^{37}$, and $R^{38}$, preferred are methoxy, ethoxy and isopropoxy.

The "—CO-alkyl" means an alkylcarbonyl group having the above-defined "alkyl group" as the alkyl moiety. Examples thereof include acetyl group, propionyl group, butyryl group, isobutyryl group, valeryl group, isovaleryl group, pivaloyl group, pentanoyl group, hexanoyl group and the like. It is preferably an alkylcarbonyl group wherein the alkyl moiety is a straight chain or branched chain alkyl group having 1 to 6, more preferably 1 to 4, carbon atoms.

For $R^{12}$, $R^{13}$, $R^{14}$, $R^{25}$, $R^{35}$ and $R^{36}$, particularly preferred are acetyl, propionyl, butyryl and isobutyryl.

The "—CO—O-alkyl" means an alkoxycarbonyl group having the above-defined "alkyl group" as the alkyl moiety. Examples thereof include methoxycarbonyl group, ethoxycarbonyl group, propoxycarbonyl group, isopropoxycarbonyl group, butoxycarbonyl group, isobutoxycarbonyl group, sec-butoxycarbonyl group, tert-butoxycarbonyl group, pentoxycarbonyl group, isopentoxycarbonyl group, neopentoxycarbonyl group, tert-pentoxycarbonyl group, 1-ethylpropoxycarbonyl group, hexyloxycarbonyl group and the like. It is preferably an alkoxycarbonyl group wherein the "alkyl moiety" is a straight chain or branched chain alkyl group having 1 to 6, more preferably 1 to 4, carbon atoms.

For $R^1$, $R^{35}$ and $R^{36}$, particularly preferred are methoxycarbonyl, ethoxycarbonyl, propoxycarbonyl, isopropoxycarbonyl and tert-butoxycarbonyl.

The "—NH-alkyl" means an alkylamino group having the above-defined "alkyl group" as the alkyl moiety. Examples thereof include methylamino group, ethylamino group, propylamino group, isopropylamino group, butylamino group, isobutylamino group, sec-butylamino group, tert-butylamino group, pentylamino group, isopentylamino group, tert-pentylamino group, hexylamino group and the like. It is preferably an alkylamino group wherein the alkyl moiety is a straight chain or branched chain alkyl group having 1 to 6, more preferably 1 to 4, carbon atoms.

For $R^{17}$, $R^{23}$ and $R^{30}$, particularly preferred are methylamino, ethylamino, propylamino and isopropylamino.

The "—N(-alkyl)$_2$" means a dialkylamino group having the above-defined "alkyl group" as the alkyl moiety. Examples thereof include dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like. It is preferably a dialkylamino group wherein the alkyl moiety is a straight chain or branched chain alkyl group having 1 to 6, more preferably 1 to 4, carbon atoms.

For $R^{17}$, $R^{23}$ and $R^{30}$, particularly preferred are dimethylamino, diethylamino and N-ethyl-N-methylamino.

The "alkyl group" and "alkoxy group" are optionally substituted by 1 to 5 substituents each independently selected from halogen atom, —CF$_3$, —OH, alkoxy group, haloalkoxy group, —N($R^{11}$)($R^{12}$) ($R^{11}$ and $R^{12}$ are each independently hydrogen atom, alkyl group or —CO-alkyl), —CN, —NO$_2$, cycloalkyl group, alkenyl group, —CO—$R^{13}$ ($R^{13}$ is —OH, alkoxy group, alkyl group or —N($R^{14}$)($R^{15}$) wherein $R^{14}$ and $R^{15}$ are each independently hydrogen atom or alkyl group), aryl group and heteroaryl group. Here, the substituent "aryl group" and "heteroaryl group" are optionally substituted by 1 to 3 substituents each independently selected from halogen atom, haloalkyl group, alkyl group, —(CH$_2$)$_n$—OH (n=0-3), —N($R^{11}$)($R^{12}$) ($R^{11}$ and $R^{12}$ are independently hydrogen atom, alkyl group or —CO-alkyl), —CN, —NO$_2$, alkoxy group, cycloalkyl group, alkenyl group, —CO—$R^{13}$ ($R^{13}$ is —OH, alkoxy group, alkyl group or —N($R^{14}$)($R^{15}$) wherein $R^{14}$ and $R^{15}$ are each independently hydrogen atom or alkyl group), aryl group and heteroaryl group.

The "alkyl group" for $R^{17}$, $R^{20}$, $R^{21}$ and the "alkoxy group" for $R^{17}$ are optionally substituted by substituents each independently selected from —OH, —SO$_2$—$R^{22}$ ($R^{22}$ is an alkyl group or —NH$_2$, and $R^{23}$ is an alkyl group, —NH-alkyl, —N(-alkyl)$_2$, or —NH$_2$ wherein the alkyl groups are optionally substituted by substituents each independently selected from —OH, an alkoxy group or —(CH$_2$)$_u$—N($R^{24}$)($R^{25}$)) (u is 0-3, $R^{24}$ and $R^{25}$ are each independently a hydrogen atom, an alkyl group or —CO-alkyl) and —(CH$_2$)$_t$—CO—$R^{23}$ (t is 0-3).

The "alkyl group" for $R^{22}$ and $R^{23}$ are optionally substituted by substituents each independently selected from —OH, an alkoxy group or —(CH$_2$)$_u$, —N($R^{24}$)($R^{25}$)) (u is 0-3, $R^{24}$ and $R^{25}$ are each independently a hydrogen atom, an alkyl group or —CO-alkyl) and —(CH$_2$)$_t$—CO—$R^{23}$ (t is 0-3).

The "alkyl" moieties of the "haloalkyl group" for $R^6$, $R^7$, $R^{26}$, $R^{27}$, $R^{28}$, $R^{31}$ and $R^{32}$, "alkylcarbonyl group" for $R^{12}$, $R^{13}$, $R^{24}$, $R^{25}$, $R^{35}$ and $R^{36}$, "alkyloxycarbonyl group" for $R^1$, $R^{35}$ and $R^{36}$, "alkylamino group" for $R^{30}$ and "dialkylamino group" for $R^{30}$ are optionally substituted by 1 to 5 substituents each independently selected from a halogen atom, a haloalkyl group, —OH, —NH$_2$, an alkoxy group, a cycloalkyl group, an alkenyl group, —COOH, —CO—O-alkyl, —CO—N($R^{10}$)($R^{11}$) ($R^{10}$ and $R^{10}$ are each independently a hydrogen atom or an alkyl group), an aryl group and a heteroaryl group. Here, the substituent "aryl group" and "heteroaryl group" are optionally substituted by 1 to 3 substituents each independently selected from a halogen atom, a haloalkyl group, an alkyl group, —(CH$_2$)$_h$—OH (h is 0-3), —N($R^{12}$)($R^{13}$) ($R^{12}$ and $R^{13}$ are each independently a hydrogen atom, an alkyl group or —CO-alkyl), —CN, —NO$_2$, an alkoxy group, a cycloalkyl group, an alkenyl group, —CO—$R^{14}$ ($R^{14}$ is —OH, an alkoxy group, an alkyl group or —N($R^{15}$)($R^{16}$) wherein $R^{15}$ and $R^{16}$ are each independently a hydrogen atom or an alkyl group), an aryl group and a heteroaryl group.

The "alkyl" moieties of the "alkylamino group" for $R^{17}$ and "dialkylamino group" for $R^{17}$ are optionally substituted by substituents each independently selected from —OH, —SO$_2$—$R^{22}$ ($R^{22}$ is an alkyl group or —NH$_2$, and $R^{23}$ is an alkyl group, —NH-alkyl, —N(-alkyl)$_2$, or —NH$_2$ wherein the alkyl groups are optionally substituted by substituents each independently selected from —OH, an alkoxy group or —(CH$_2$)$_u$—N($R^{24}$)($R^{25}$)) (u is 0-3, $R^{24}$ and $R^{25}$ are each independently a hydrogen atom, an alkyl group or —CO-alkyl) and —(CH$_2$)$_t$—CO—$R^{23}$ (t is 0-3).

The "alkyl" moieties of the "alkylamino group" for $R^{23}$ and "dialkylamino group" for $R^{23}$ are optionally substituted by substituents each independently selected from —OH, an alkoxy group or —(CH$_2$)$_u$—N($R^{24}$)($R^{25}$)) (u is 0-3, $R^{24}$ and $R^{25}$ are each independently a hydrogen atom, an alkyl group or —CO-alkyl) and —(CH$_2$)$_t$CO—$R^{23}$ (t is 0-3).

The "aryl group" and the "heteroaryl group" are optionally substituted by 1 to 3 substituents each independently selected from a halogen atom, a haloalkyl group, an alkyl group, —(CH$_2$)$_h$—OH (h is 0-3), —N($R^{12}$)($R^{13}$) ($R^{12}$ and $R^{13}$ are each independently a hydrogen atom, an alkyl group or —CO-alkyl), —CN, —NO$_2$, an alkoxy group, a cycloalkyl group, an alkenyl group, —CO—$R^{14}$ ($R^{14}$ is —OH, an alkoxy group, an alkyl group or —N($R^{15}$)($R^{16}$) wherein $R^{15}$ and $R^{16}$ are each independently a hydrogen atom or an alkyl group), an aryl group and a heteroaryl group.

The "cycloalkyl group" for $R^6$, $R^7$, $R^{27}$, $R^{28}$, $Y^1$ and $Y^2$ and "heterocycloalkyl group" for $Y^1$ and $Y^2$ are optionally substituted by 1 to 3 substituents each independently selected from a halogen atom, a haloalkyl group, an alkyl group, —(CH$_2$)$_h$—OH (h is 0-3), —N($R^{12}$)($R^{13}$) ($R^{12}$ and $R^{13}$ are each independently a hydrogen atom, an alkyl group or —CO-alkyl), —CN, —NO$_2$, an alkoxy group, a cycloalkyl group, an alkenyl group, —CO—$R^{14}$ ($R^{14}$ is —OH, an alkoxy group, an alkyl group or —N($R^{15}$)($R^{16}$) wherein $R^{15}$ and $R^{16}$ are each independently a hydrogen atom or an alkyl group), an aryl group and a heteroaryl group.

The "cycloalkyl group" for $R^1$, $R^2$, $R^3$, $R^4$ and $R^5$ are optionally substituted by 1 to 5 substituents each independently selected from a halogen atom, a haloalkyl group, —OH, —NH$_2$, an alkoxy group, a cycloalkyl group, an alkenyl group, —COOH, —CO—O-alkyl, —CO—N(R$^{10}$)(R$^{11}$) (R$^{10}$ and R$^{11}$ are each independently a hydrogen atom or an alkyl group), an aryl group and a heteroaryl group. Here, the substituent "aryl group" and "heteroaryl group" are optionally substituted by 1 to 3 substituents each independently selected from a halogen atom, a haloalkyl group, an alkyl group, —(CH$_2$)$_h$—OH (h is 0-3), —N(R$^{12}$)(R$^{13}$) (R$^{12}$ and R$^{13}$ are each independently a hydrogen atom, an alkyl group or —CO-alkyl), —CN, —NO$_2$, an alkoxy group, a cycloalkyl group, an alkenyl group, —CO—R$^{14}$ (R$^{14}$ is —OH, an alkoxy group, an alkyl group or —N(R$^{15}$)(R$^{16}$) wherein R$^{15}$ and R$^{16}$ are each independently a hydrogen atom or an alkyl group), an aryl group and a heteroaryl group.

The above-mentioned substituents "alkyl group", "cycloalkyl group", "heterocycloalkyl group", "alkenyl group", "aryl group", "heteroaryl group", "halogen atom", "haloalkyl group", "alkoxy group", "haloalkoxy group" are as defined above.

R$^8$ and R$^9$ in combination may form —O-alkylene-O—. Here, the "alkylene" means a divalent hydrocarbon. Examples thereof include methylene, ethylene, propylene, butylene, pentylene, hexylene and the like. It is preferably an alkylene having 1 to 6, more preferably 1 to 4, carbon atoms, particularly preferably methylene.

In the above-mentioned formulae, m is preferably 0; R$^2$ and R$^3$ are preferably in combination to form a Y$^1$ ring, which is a C$_{3-8}$ cycloalkane group; Ar$^1$ is preferably a phenyl group; R$^6$ and R$^7$ are preferably independently a halogen atom or a hydrogen atom.

The "pharmaceutically acceptable salt" may be any salt as long as it forms a non-toxic salt with a pyrazole compound represented by the above-mentioned formula. For example, it can be obtained by reaction with inorganic acids such as hydrochloric acid, sulfuric acid, phosphoric acid, hydrobromic acid and the like; organic acids such as oxalic acid, malonic acid, citric acid, fumaric acid, lactic acid, malic acid, succinic acid, tartaric acid, acetic acid, trifluoroacetic acid, gluconic acid, ascorbic acid, methylsulfonic acid, benzylsulfonic acid and the like; inorganic bases such as sodium hydroxide, potassium hydroxide, calcium hydroxide, magnesium hydroxide, ammonium hydroxide and the like; organic bases such as methylamine, diethylamine, triethylamine, triethanolamine, ethylenediamine, tris(hydroxymethyl)methylamine, guanidine, choline, cinchonine, N-methyl-D-glucamine and the like; or amino acids such as lysin, histidine, arginine, alanine and the like. In the present invention, a water-containing form, a hydrate and a solvate of each compound are also encompassed therein.

In addition, the pyrazole compound represented by the above-mentioned formula includes various isomers. For example,

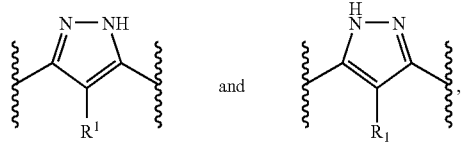

forms are present as tautomers, and when an asymmetric carbon atom is present, enantiomers and diastereomers are present as stereoisomers based thereon. In some cases, geometric isomers may be present. Accordingly, the present invention encompasses all these isomers and mixtures thereof.

The present invention also encompasses prodrugs and metabolites of the pyrazole compound represented by the formula. A "prodrug" is a derivative of the compound of the present invention, which has a chemically or metabolically decomposable group, which, after being administered to a living organism, is restored to its original compound form and exhibits its intrinsic efficacy, and which includes complexes and salts free of a covalent bond. For example, ester derivatives known as prodrugs in the field of pharmaceutical agents can be used.

When the compound of the present invention is used as a pharmaceutical preparation, it is generally admixed with a pharmaceutically acceptable carrier, excipient, diluent, extender, disintegrant, stabilizer, preservative, buffer, emulsifier, fragrance, coloring agent, sweetening agent, thickening agent, corrigent, dissolution aids and other additives known per se, such as water, vegetable oil, alcohols such as ethanol, benzyl alcohol and the like, polyethylene glycol, glycerol triacetate, gelatin, lactose, carbohydrates such as starch and the like, magnesium stearate, talc, lanolin, vaseline and the like, and produced in the form of tablet, pill, powder, granule, suppository, injection, eye drop, liquid, capsule, troche, aerosol, elixir, suspension, emulsion, syrup and the like by a conventional method for systemic or local, oral or parenteral administration.

While the dose of the compound of the present invention varies depending on the age, body weight, symptom, disease to be treated, administration method and the like, it is generally 1 mg to 1000 mg for an adult per administration, which is given once to several times a day.

The compound of the present invention can be administered to a mammal (human, mouse, rat, rabbit, dog, cat, bovine, pig, monkey etc.) as an HSD1 inhibitor, a prophylactic or therapeutic drug of diabetes, a prophylactic or therapeutic drug of diabetic complication (retinopathy, nephropathy, neuropathy, cardiac infarction and cerebral infarction based on arteriosclerosis etc.), a prophylactic or therapeutic drug of hyperlipemia, a prophylactic or therapeutic drug of obesity, neurodegenerative disease and the like, or a prophylactic or therapeutic drug of diseases mediated by HSD1.

The compound of the present invention can be administered to a mammal concurrently with other therapeutic drug of diabetes or obesity with the aim of the prophylaxis or treatment of diabetes. In the present invention, the "therapeutic drug of diabetes" encompasses therapeutic drugs of diabetic complications. Furthermore, the compound of the present invention can be administered in combination with other therapeutic drugs of diabetes or obesity to a mammal for the prophylaxis or treatment of obesity.

In the case of a combined administration, the compound of the present invention may be administered simultaneously with other therapeutic drugs of diabetes or other therapeutic drugs of obesity (hereinafter to be referred to as a combined pharmaceutical agent) or may be administered at time intervals. In the case of a combined administration, a pharmaceutical composition containing the compound of the present invention and a combined pharmaceutical agent can be administered. Alternatively, a pharmaceutical composition containing the compound of the present invention and a pharmaceutical composition containing a combined pharmaceutical agent may be administered separately. The administration routes of respective pharmaceutical compositions may be the same or different.

In the case of a combined administration, the compound of the present invention may be administered at a dose of 1 mg to 1000 mg per administration, which is given once to several times a day. In addition, the compound may be administered at a smaller dose. The combined pharmaceutical agent can be administered at a dose generally employed for the prophylaxis or treatment of diabetes or obesity or at a smaller dose than that.

As other therapeutic drug of diabetes to be used for the combined administration, insulin preparation, sulfonylurea, insulin secretagogue, sulfonamide, biguanide, α-glucosidase inhibitor, PTP1B inhibitor, insulin sensitizer and the like can be mentioned. For example, insulin, glibenclamide, tolbutamide, glyclopyramide, acetohexamide, glimepiride, tolazamide, gliclazide, nateglinide, glybuzole, metformin hydrochloride, buformine hydrochloride, voglibose, acarbose, pioglitazone hydrochloride and the like can be used for combined administration with the compound of the present invention.

As other therapeutic drug of obesity to be used for the combined administration, for example, mazindol can be mentioned.

One example of the production method of the pyrazole compound of the present invention is described in the following, which does not limit the production method of the compound of the present invention. Even in the absence of description in the production method, efficient production can be afforded by introducing, where necessary, a protecting group into a functional group followed by deprotection in a subsequent step, exchanging the order of respective production methods and steps, and the like. The post-reaction treatment can be applied by a typical method by selecting or combining conventional methods as necessary, such as isolation and purification, crystallization, recrystallization, silica gel chromatography, preparative HPLC and the like.

Production Method 1

In this production method, a pyrazole compound is produced, and the method includes any of the following steps.

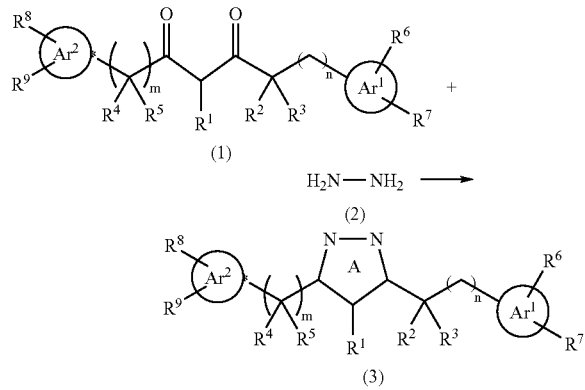

wherein each symbol is as defined above.

Diketone (1) synthesized by a known method and hydrazine hydrate (2) are reacted in a solvent to give pyrazole (3). As the solvent, methanol, ethanol, n-propanol, isopropanol, acetonitrile, diethyl ether, tetrahydrofuran (THF), acetic acid, 1,4-dioxane, N,N-dimethylformamide, dimethyl sulfoxide, dichloromethane, 1,2-dichloroethane, chloroform, benzene, chlorobenzene, o-dichlorobenzene, toluene, xylene, pyridine, acetic acid, or a mixed solvent thereof can be mentioned. The reaction temperature is preferably 20° C.-250° C.

EXAMPLES

The pyrazole compound represented by the formula of the present invention and the production method thereof are explained in detail in the following by referring to Examples, which are not to be construed as limitative.

Example 1-1

Production of 3-(2,4-dichlorophenyl)-4-methyl-5-((1-phenylcyclopropane)-1-yl)-pyrazole 1-(2,4-dichlorophenyl)-2-methyl-3-(1-phenylcyclopropane)-propane-1,3-dione (347 mg) were suspended in acetic acid (4 mL) and ethanol (2 mL), hydrazine hydrate (100 mg) was added and the mixture was heated for 3 hours at 80° C. The reaction solution was concentrated and extracted with ethyl acetate. The ethyl acetate layer was washed successively with saturated brine, dried over anhydrous sodium sulfate, and concentrated to dryness. The obtained residue was purified by silica gel chromatography (n-hexane:ethyl acetate=3:1) and dried to give the title compound (318 mg).

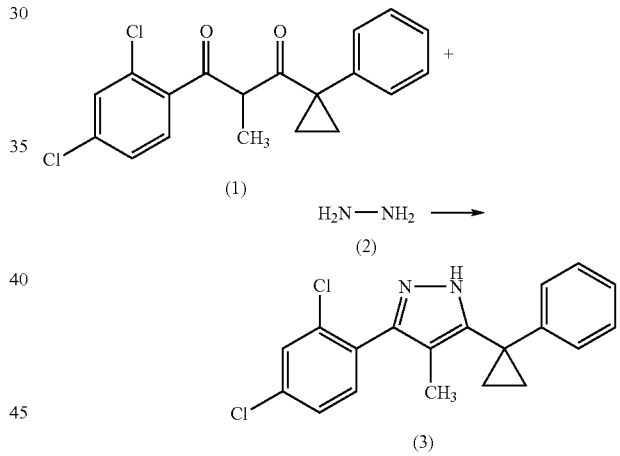

Examples 1-2 to 1-16

In the same manner as in Example 1-1, and using other conventional methods as necessary, a pyrazole compound was produced. The structural formula and property values of each Example compound are shown in the following Table.

| Example | Molecular Structure | $^1$H-NMR |
|---------|---------------------|-----------|
| Ex. 1-1 | ![structure] | (300 MHz, DMSO-D6), 1.25-1.35(4H, m), 1.80(3H, s), 7.05-7.35(5H, m), 7.37-7.55(2H, m), 7.72(1H, s), 12.9(1H, brs) |

-continued

| Example | Molecular Structure | ¹H-NMR |
|---|---|---|
| Ex. 1-2 | 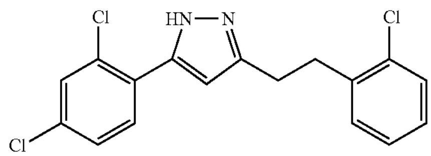 | (300 MHz, DMSO-D6), 2.93-3.12(4H, m), 6.54(1H, s), 7.19-7.48(5H, m), 7.66(1H, d, J = 1.6 Hz), 7.77(1H, d, J = 8.3 Hz), 12.9(1H, brs) |
| Ex. 1-3 | 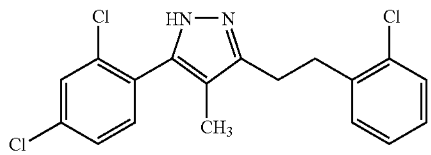 | (300 MHz, CDCl3), 1.83(3H, s), 2.93-2.97(2H, m), 3.06-3.11(2H, m), 7.11-7.18(3H, m), 7.27-7.38(3H, m), 7.48-7.49(1H, m) |
| Ex. 1-4 | 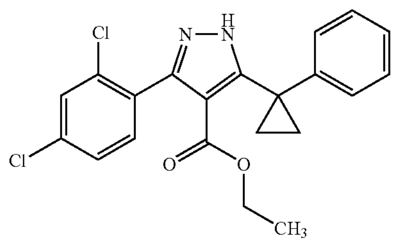 | (300 MHz, DMSO-D6), 0.82-0.94(3H, m), 1.33-1.43(4H, m), 3.83-4.01(2H, m), 7.09-7.32(5H, m), 7.37-7.53(2H, m), 7.59-7.75(1H, m), 13.7(1H, brs) |
| Ex. 1-5 | 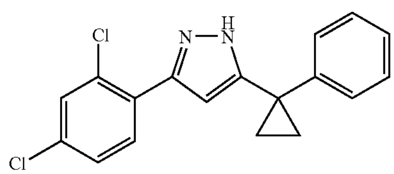 | (300 MHz, DMSO-D6), 1.23-1.39(4H, m), 6.48(1H, brs), 7.13-7.39(5H, m), 7.40-7.54(1H, m), 7.61-7.72(1H, m), 7.72-7.90(1H, m), 13.0(1H, brs) |
| Ex. 1-6 | 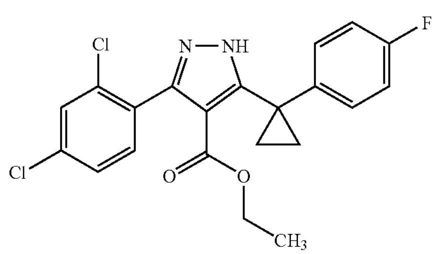 | (300 MHz, DMSO-D6), 0.96(3H, t, J = 7.0 Hz), 4.00(2H, q, J = 7.0 Hz), 4.26(2H, s), 7.04-7.76(7H, m), 13.5(1H, brs) (300 MHz, DMSO-D6), 0.96(3H, t, J = 7.0 Hz), 4.00(2H, q, J = 7.0 Hz), 4.26(2H, s), 7.04-7.76(7H, m), 13.5(1H, brs) |
| Ex. 1-7 | 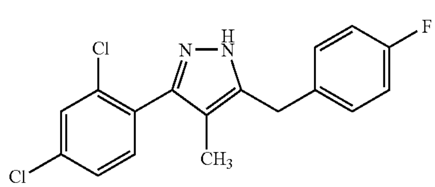 | (300 MHz, DMSO-D6), 1.12-1.33(4H, m), 1.86-2.22(4H, m), 1.90(3H, s), 2.85-3.53(5H, m), 4.38-4.59(2H, m), 7.07-7.30(5H, m), 7.60(1H, dd, J = 8.5, 2.2 Hz), 7.80(1H, d, J = 2.2 Hz), 7.98(1H, d, J = 8.5 Hz), 10.8(1H, brs) |
| Ex. 1-8 | 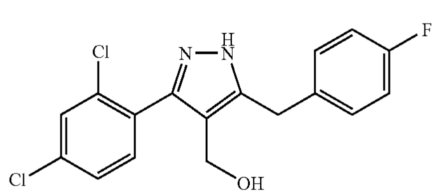 | (300 MHz, DMSO-D6), 3.94-4.08(2H, m), 4.14-4.30(2H, m), 4.68(1H, t, J = 5.0 Hz), 7.05-7.81(7H, m), 12.7 and 12.8(1H, each brs) |

-continued
| Example | Molecular Structure | ¹H-NMR |
|---|---|---|
| Ex. 1-9 | 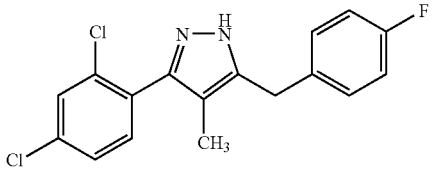 | (300 MHz, DMSO-D6), 1.41(3H, s), 2.98(1H, d, J = 15 Hz), 3.01(1H, d, J = 15 Hz), 6.80-7.77(7H, m), 11.7(1H, brs) |
| Ex. 1-10 | 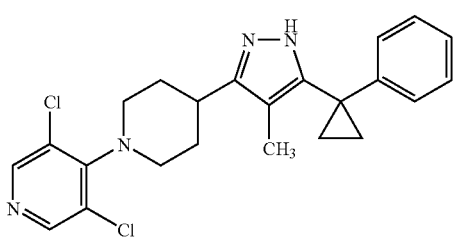 | (300 MHz, DMSO-D6), 1.32-1.41(4H, m), 1.80-2.03(4H, m), 1.98(3H, s), 2.94-3.10(1H, m), 3.28-3.49(4H, m), 7.14-7.23(3H, m), 7.26-7.33(2H, m), 8.46(1H, s), 8.47(1H, s) |
| Ex. 1-11 | 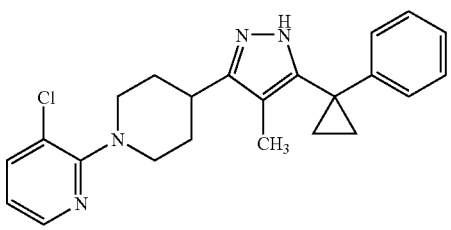 | (300 MHz, DMSO-D6), 1.10-1.33(4H, m), 1.74-1.98(4H, m), 1.84(3H, s), 2.67-2.96(3H, m), 3.69-3.91(2H, m), 6.91-7.31(6H, m), 7.78(1H, d, J = 7.7 Hz), 8.21(1H, d, J = 4.8 Hz), 12. 0 and 12.3(1H, each s) |
| Ex. 1-12 | 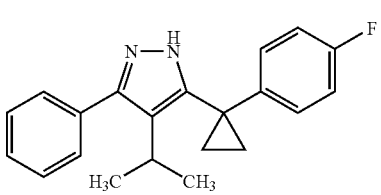 | (400 MHz, CDCl3), 0.97(6H, d, J = 7.19 Hz), 1.26-1.32(2H, m), 1.42-1.47(2H, m), 3.04(1H, septet, J = 7.19 Hz), 6.89-6.96(3H, m), 7.05-7.10(1H, m), 7.35-7.44(5H, m) |
| Ex. 1-13 | 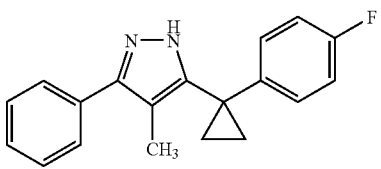 | (300 MHz, DMSO-D6), 1.18-1.34(4H, m), 1.73 and 1.82(3H, each s), 7.02-7.22(4H, m), 7.34-7.62(4H, m), 12.6 and 12.9(1H, each s) |
| Ex. 1-14 | 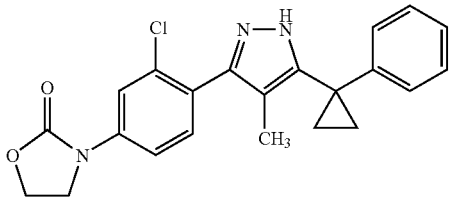 | (300 MHz, DMSO-D6), 1.20-1.36(4H, m), 1.84 and 1.91(3H, each s), 4.08(2H, t, J = 9.0 Hz), 4.44(2H, t, J = 9.0 Hz), 7.08-7.20(3H, m), 7.22-7.30(2H, m), 7.50-7.66(3H, m), 12.6 and 12.9(1H, each s) |
| Ex. 1-15 | 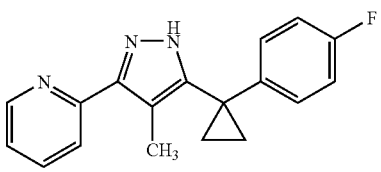 | (400 MHz, DMSO-D6), 1.22-1.35(4H, m), 2.14 and 2.26(3H, each s), 6.99-7.17(4H, m), 7.18-7.32(1H, m), 7.72-7.94(2H, m), 8.49-8.63(1H, m), 12.9(1H, brs) |

| Example | Molecular Structure | $^1$H-NMR |
|---|---|---|
| Ex. 1-16 | 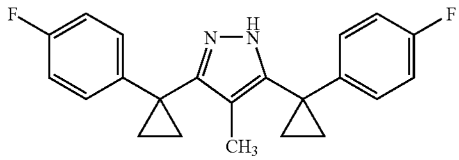 | (400 MHz, DMSO-D6), 1.08-1.36(8H, m), 1.72(3H, s), 6.98-7.16(8H, m), 7.37-7.55(2H, m), 12.4(1H, brs) |

Experimental Example

In Vitro HSD1 (Hydroxysteroid Dehydrogenase 1) Activity Inhibitory Action

The HSD1 inhibitory activity was examined by quantitative determination by an SPA (scintillation proximity assay) system of the suppressive action on the conversion from cortisone to cortisol using human HSD1 (hereinafter recombinant HSD1) expressed using a baculo-virus system as an enzyme source. For the reaction, a reagent was added to a 96 well plate (96 well Opti-plates™-96 (Packard)) to the following final concentration and a volume of 100 μl was reacted at room temperature for 90 min. The reaction solution used was 0.1 μg/mL recombinant HSD1, 500 μM NADPH, 16 nM $^3$H cortisone (Amersham Biosciences, 1.78 Tbq/mol) dissolved in 0.1% BSA (Sigma)-containing PBS and the test drug was 2 μl of a compound solution (dissolved in DMSO). After 90 min, the reaction was stopped by adding PBS (40 μl, containing 0.1% BSA (Sigma)) containing 0.08 μg of anti-cortisol mouse monoclonal antibody (East Coast Biologics), 365 μg SPA PVT mouse antibody-binding beads (Amersham Biosciences) and 175 μM carbenoxolone (Sigma) to the reaction solution. After the completion of the reaction, the plate was incubated overnight at room temperature and the radioactivity was measured by Topcount (Packard). For control, the value (0% inhibition) of the well containing 2 μl of DMSO instead of the test drug was used, and for positive control, the value (100% inhibition) of the well containing carbenoxolone instead of the test drug at the final concentration of 50 μM was used. The inhibition (%) of the test drug was calculated by ((value of control−value of test drug)/(value of control−value of positive control))×100 (%). The $IC_{50}$ value was analyzed using a computer-based curve fitting soft. The obtained results are shown in the following Table.

| Examples | Human HSD1 $IC_{50}$ |
|---|---|
| Ex. 1-1 | ++ |
| Ex. 1-2 | + |
| Ex. 1-3 | ++ |
| Ex. 1-4 | + |
| Ex. 1-5 | + |
| Ex. 1-6 | + |
| Ex. 1-7 | + |
| Ex. 1-8 | + |
| Ex. 1-9 | + |
| Ex. 1-10 | + |
| Ex. 1-11 | ++ |
| Ex. 1-12 | ++ |
| Ex. 1-13 | ++ |
| Ex. 1-14 | + |
| Ex. 1-15 | ++ |
| Ex. 1-16 | ++ |

In the above Table,
"+" in the column of $IC_{50}$ means 10 nM ≤ $IC_{50}$ < 1,000 nM and
"++" in the column of $IC_{50}$ means $IC_{50}$ < 10 nM.

In the above Table, "+" in the column of $IC_{50}$ means 10 nM≦$IC_{50}$<1,000 nM and "++" in the column of $IC_{50}$ means $IC_{50}$<10 nM.

Examples 2-1 to 2-45

In the same manner as in Example 1-1, and using other conventional methods as necessary, the pyrazole compounds shown in the following Table can be also produced.

| Ex. 2-1 | 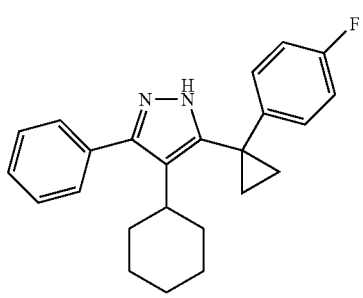 |
|---|---|

-continued
Ex. 2-2
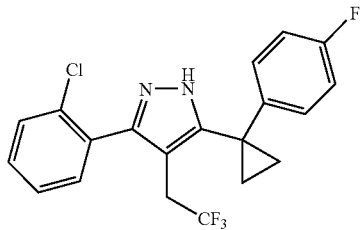
Ex. 2-3
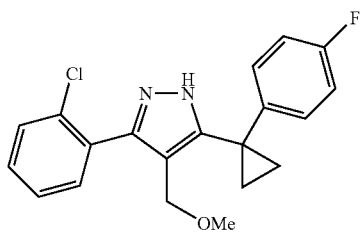
Ex. 2-4
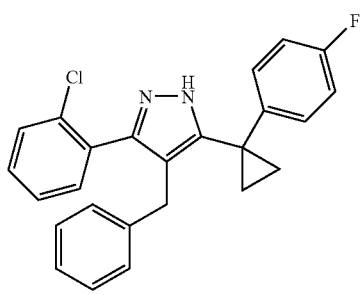
Ex. 2-5
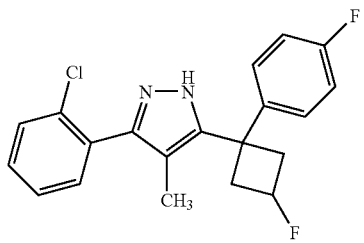
Ex. 2-6
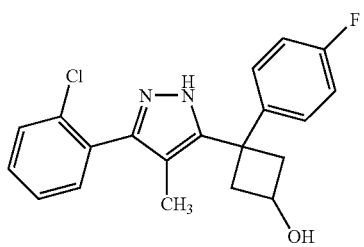
Ex. 2-7
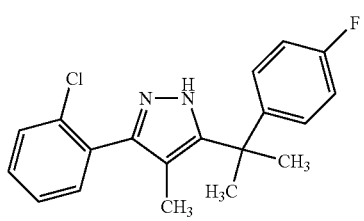

-continued
Ex. 2-8 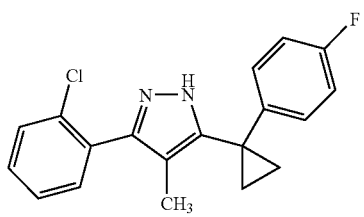
Ex. 2-9 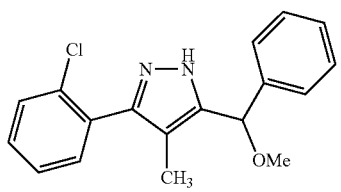
Ex. 2-10 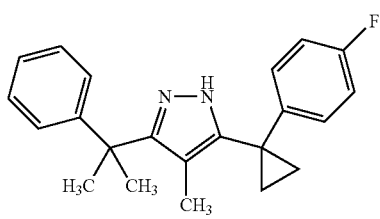
Ex. 2-11 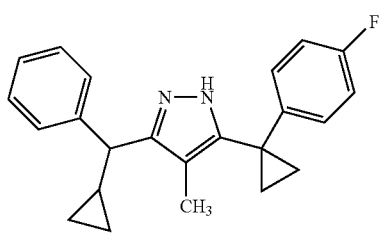
Ex. 2-12 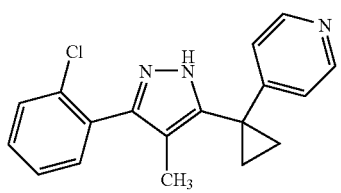
Ex. 2-13 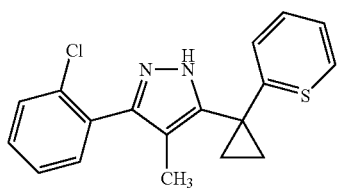
Ex. 2-14 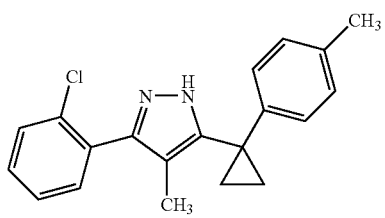

-continued
Ex. 2-15 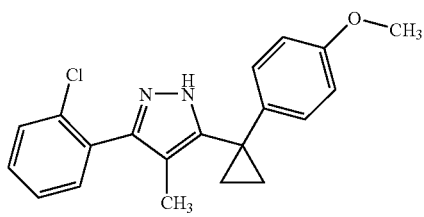
Ex. 2-16 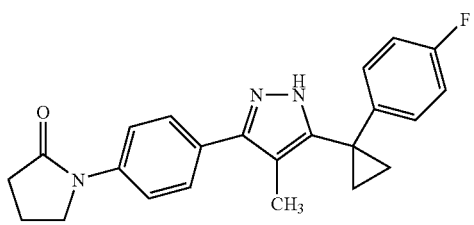
Ex. 2-17 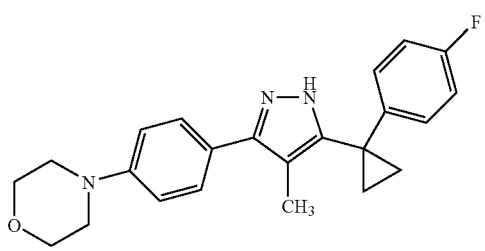
Ex. 2-18 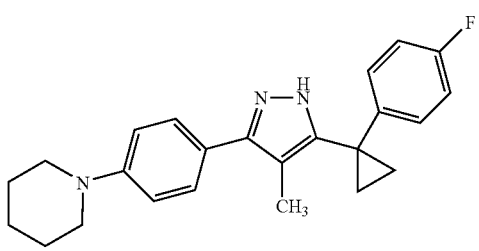
Ex. 2-19 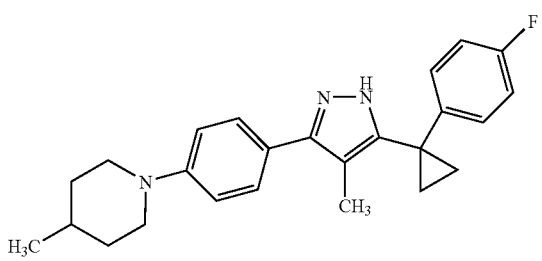
Ex. 2-20 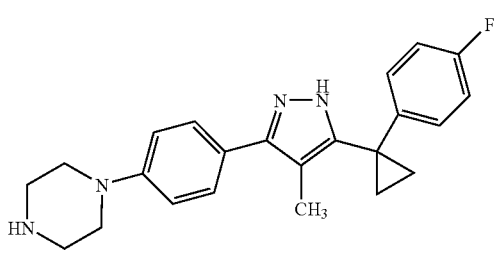

-continued
Ex. 2-21
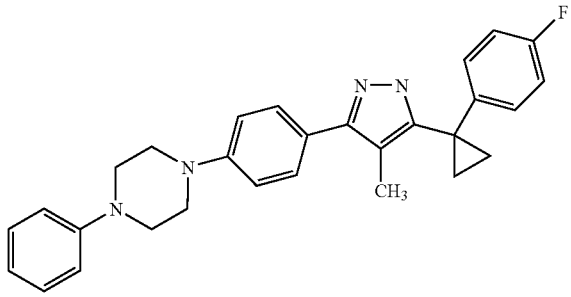
Ex. 2-22
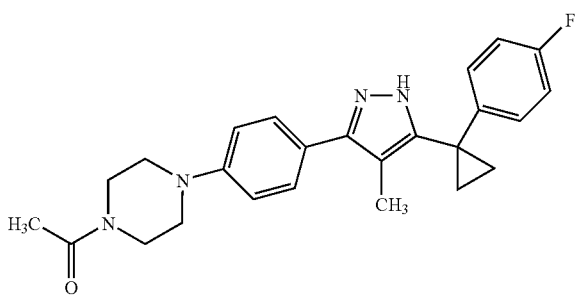
Ex. 2-23
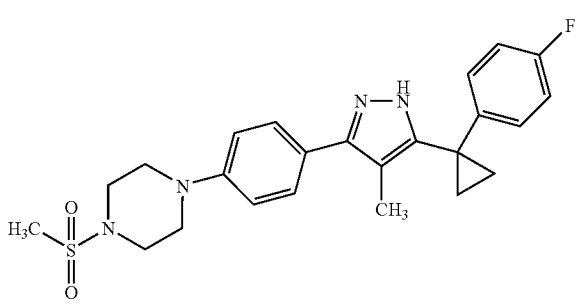
Ex. 2-24
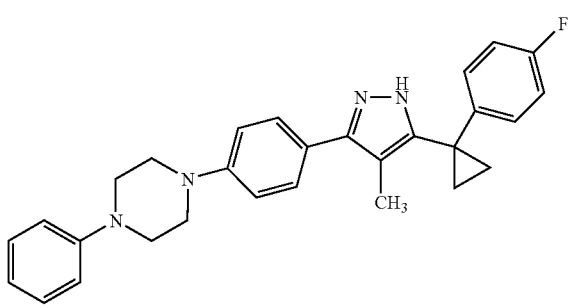
Ex. 2-25
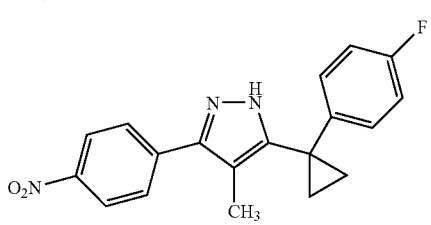
Ex. 2-26
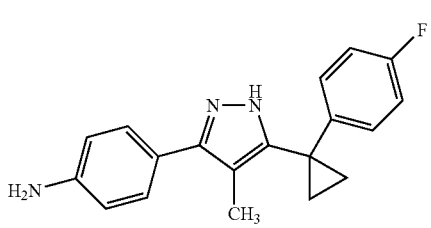

-continued
Ex. 2-27
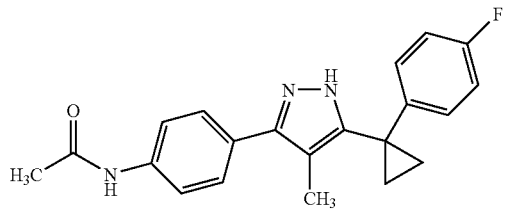
Ex. 2-28
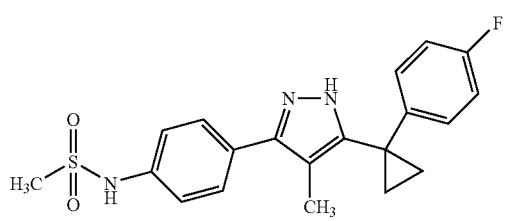
Ex. 2-29
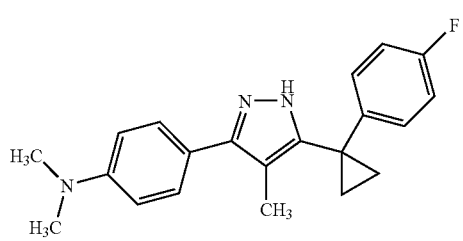
Ex. 2-30
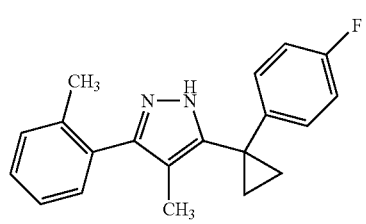
Ex. 2-31
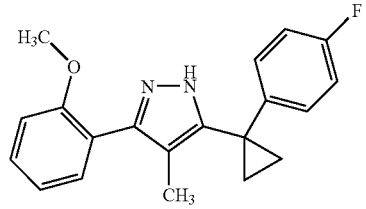
Ex. 2-32
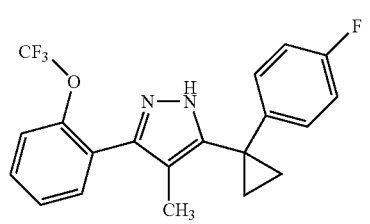
Ex. 2-33
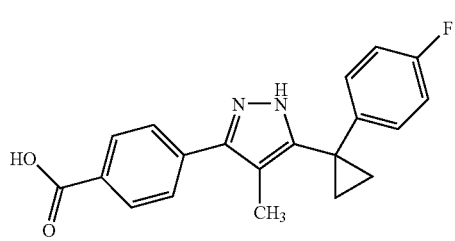

-continued
Ex. 2-34
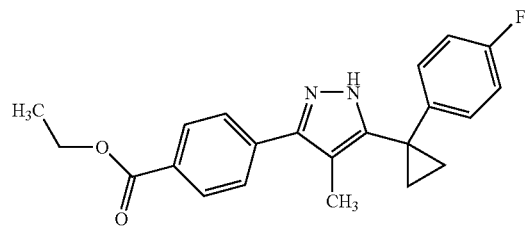
Ex. 2-35
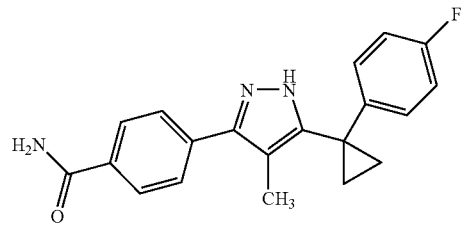
Ex. 2-36
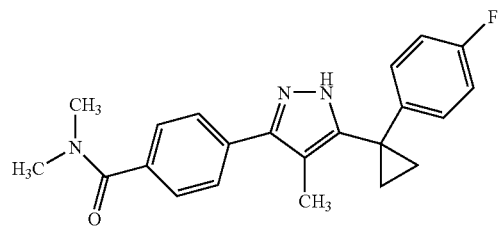
Ex. 2-37
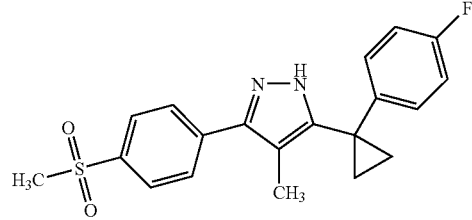
Ex. 2-38
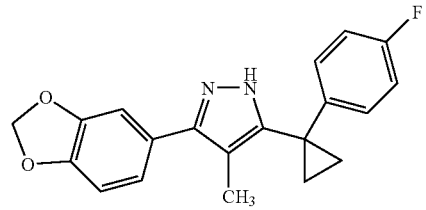
Ex. 2-39
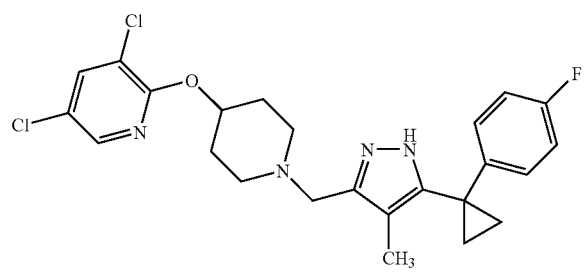

-continued
Ex. 2-40
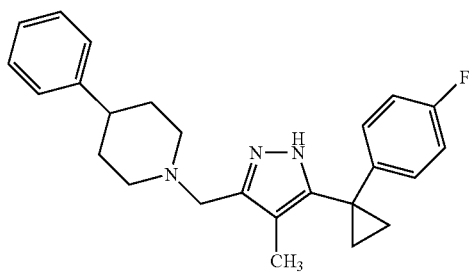
Ex. 2-41
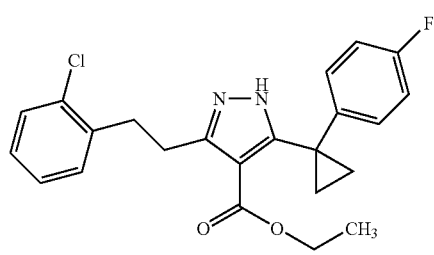
Ex. 2-42
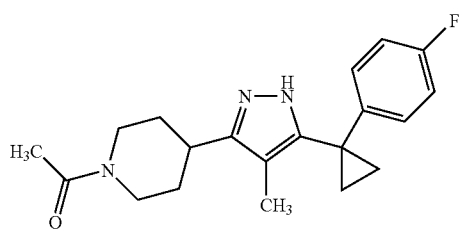
Ex. 2-43
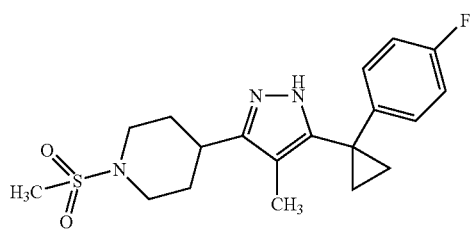
Ex. 2-44
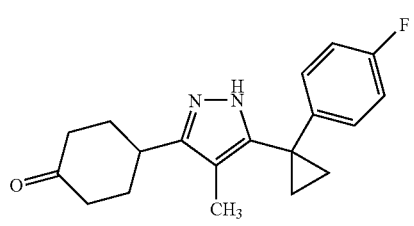
Ex. 2-45
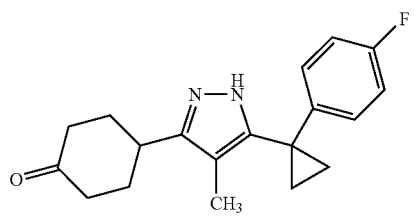

What is claimed is:

1. A pyrazole compound represented by the following formula:

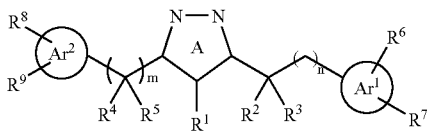

wherein $R^1$ is —CO—O-alkyl, —COOH, an alkyl group, an alkoxy group or a cycloalkyl group,
wherein the alkyl group, the alkoxy group and the cycloalkyl group are optionally substituted by 1 to 5 substituents each independently selected from a halogen atom, a haloalkyl group, —OH, —NH$_2$, an alkoxy group, a cycloalkyl group, an alkenyl group, —COOH, —CO—O-alkyl, —CO—N($R^{10}$)($R^{11}$), —N($R^{10}$)—CO—$R^{11}$, an aryl group and a heteroaryl group,
wherein each $R^{10}$ and $R^{11}$ is independently a hydrogen atom or an alkyl group, and the aryl group and the heteroaryl group are optionally substituted by 1 to 3 substituents each independently selected from a halogen atom, a haloalkyl group, an alkyl group, —(CH$_2$)$_h$—OH, —N($R^{12}$)($R^{13}$), —CN, —NO$_2$, an alkoxy group, a cycloalkyl group, an alkenyl group, —CO—$R^{14}$, an aryl group and a heteroaryl group,
wherein the subscript h is an integer of from 0 to 3, $R^{12}$ and $R^{13}$ in each instance are independently a hydrogen atom, an alkyl group or —CO-alkyl, and each $R^{14}$ is independently —OH, an alkoxy group, an alkyl group or —N($R^{15}$)($R^{16}$),
wherein $R^{15}$ and $R^{16}$ are each independently a hydrogen atom or an alkyl group;

$R^2$ and $R^3$ are in combination with the carbon atom to which each is attached to form a ring represented by

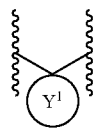

wherein the $Y^1$ ring is a C$_{3-8}$ cycloalkane group, and the wavy lines indicate the point of attachment to the remainder of the molecule;
wherein the cycloalkane and the heterocycloalkane groups are optionally substituted by 1 to 3 substituents each independently selected from a halogen atom, a haloalkyl group, an alkyl group, —(CH$_2$)$_h$—OH, —N($R^{12}$)($R^{13}$), —CN, —NO$_2$, an alkoxy group, a cycloalkyl group, an alkenyl group, —CO—$R^{14}$, an aryl group and a heteroaryl group,
wherein the alkyl group, the alkoxy group and the cycloalkyl group are optionally substituted by 1 to 5 substituents each independently selected from a halogen atom, a haloalkyl group, —OH, —NH—$_2$, an alkoxy group, a cycloalkyl group, an alkenyl group, —COOH, —CO—O-alkyl, —CO—N($R^{10}$)($R^{11}$), an aryl group and a heteroaryl group,
wherein the aryl group and the heteroaryl group are optionally substituted by 1 to 3 substituents each independently selected from a halogen atom, a haloalkyl group, an alkyl group, —(CH$_2$)$_h$—OH, —N($R^{12}$)($R^{13}$), —CN, —NO$_2$, an alkoxy group, a cycloalkyl group, an alkenyl group, —CO—$R^{14}$, an aryl group and a heteroaryl group;

$R^4$ and $R^5$ are each independently a hydrogen atom, an alkyl group, an alkoxy group, a cycloalkyl group or $R^4$ and $R^5$ in combination with the carbon atoms to which they are attached, optionally form a ring represented by

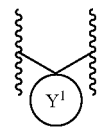

wherein the $Y^1$ ring is a cycloalkane or a heterocycloalkane,
wherein the cycloalkane and the heterocycloalkane groups are optionally substituted by 1 to 3 substituents each independently selected from a halogen atom, a haloalkyl group, an alkyl group, —(CH$_2$)$_h$—OH, —N($R^{12}$)($R^{13}$), —CN, —NO$_2$, an alkoxy group, a cycloalkyl group, an alkenyl group, —CO—$R^{14}$, an aryl group and a heteroaryl group,
wherein the alkyl group, the alkoxy group and the cycloalkyl group are optionally substituted by 1 to 5 substituents each independently selected from a halogen atom, a haloalkyl group, —OH, —NH$_2$, an alkoxy group, a cycloalkyl group, an alkenyl group, —COOH, —CO—O-alkyl, —CO—N($R^{10}$)($R^{11}$), an aryl group and a heteroaryl group,
wherein the aryl group and the heteroaryl group are optionally substituted by 1 to 3 substituents each independently selected from a halogen atom, a haloalkyl group, an alkyl group, —(CH$_2$)$_h$—OH, —N($R^{12}$)($R^{13}$), —CN, —NO$_2$, an alkoxy group, a cycloalkyl group, an alkenyl group, —CO—$R^{14}$, an aryl group and a heteroaryl group;

the subscript n is an integer of from 0;

$Ar^1$ is an aryl group;

$R^6$ and $R^7$ are each independently a hydrogen atom, a halogen atom, a haloalkyl group, an alkyl group, —(CH$_2$)$_j$—OH, —N($R^{12}$)($R^{13}$), —CN, —NO$_2$, an alkoxy group, a cycloalkyl group, an alkenyl group, —CO—$R^{14}$, an aryl group or heteroaryl group
wherein j is 0-3, and the aryl group and the heteroaryl group are optionally substituted by 1 to 3 substituents each independently selected from a halogen atom, a haloalkyl group, an alkyl group, —(CH$_2$)$_h$—OH, —N($R^{12}$)($R^{13}$), —CN, —NO$_2$, an alkoxy group, a cycloalkyl group, an alkenyl group, —CO—$R^{14}$, an aryl group and a heteroaryl group;

the subscript m is an integer of from 0;

$R^8$ and $R^9$ are each independently a hydrogen atom, a halogen atom, —OH, —NO$_2$, —CN, an alkyl group, an alkoxy group, —CO—R$^{17}$, —SO$_2$—R$^{17}$, —CO—N(R$^{18}$)(R$^{19}$), —N(R$^{20}$)(R$^{21}$) or in combination form —O-alkylene-O—, wherein the alkyl group and the alkoxy group are optionally substituted by 1 to 5 substituents each independently selected from a halogen atom, a haloalkyl group, —OH, —NH$_2$, an alkoxy group, a cycloalkyl group, an alkenyl group, —COOH, —CO—O-alkyl, —CO—N(R$^{10}$)(R$^{11}$), —N(R$^{10}$)—CO—R$^{11}$, an aryl group and a heteroaryl group, wherein the aryl group and the heteroaryl group are optionally substituted by 1 to 3 substituents each independently selected from a halogen atom, a haloalkyl group, an alkyl group, —(CH$_2$)$_h$—OH, —N(R$^{12}$)(R$^{13}$), —CN, —NO$_2$, an alkoxy group, a cycloalkyl group, an alkenyl group, —CO—R$^{14}$, an aryl group and a heteroaryl group, $R^{17}$ is —OH, an alkoxy group, an alkyl group, —NH$_2$, —NH-alkyl or —N(-alkyl)$_2$, wherein the alkoxy group and alkyl groups are optionally substituted by substituents each independently selected from —OH, —SO$_2$—R$^{22}$ and —(CH$_2$)$_t$—CO—R$^{23}$, wherein t is 0-3, R$^{22}$ is an alkyl group or —NH$_2$, and R$^{23}$ is an alkyl group, —NH-alkyl, —N(-alkyl)$_2$, or —NH$_2$, wherein the alkyl groups are optionally substituted by substituents each independently selected from —OH, an alkoxy group or —(CH$_2$)$_u$—N(R$^{24}$)(R$^{25}$)

wherein u is 0-3, and R$^{24}$ and R$^{25}$ are each independently a hydrogen atom, an alkyl group or —CO-alkyl $R^{18}$ and $R^{19}$ are each independently a hydrogen atom, an alkyl group or —(CH$_2$)$_p$—R$^{26}$, wherein p is 0-3 and R$^{26}$ is —OH, a haloalkyl group, an alkoxy group, —CO—NH$_2$ or —N(R$^{24}$)(R$^{25}$), $R^{20}$ and $R^{21}$ are each independently a hydrogen atom, an alkyl group —CO—R$^{23}$ or in combination with the nitrogen atom to which each is attached form

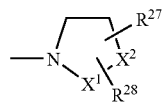

wherein the alkyl group is optionally substituted by substituents each independently selected from —OH, —SO$_2$—R$^{22}$ and —(CH$_2$)$_t$—CO—R$^{23}$, X$^1$ is —CO—, —CH$_2$— or —CH$_2$CH$_2$—, X$^2$ is —O—, —(CH$_2$)$_q$, —N(R$^{29}$)— or a spiro cyclic ring represented by

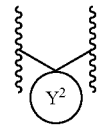

wherein q is 0-2, R$^{29}$ is a hydrogen atom, —CO—R$^{30}$, —SO$_2$—R$^{30}$ or —(CH$_2$)$_r$—Ar$^3$ wherein R$^{30}$ is an alkyl group, an alkoxy group, —NH-alkyl or —N(-alkyl)$_2$, r is 0-3, and Ar$^3$ is an aryl group or heteroaryl group, wherein the aryl group and heteroaryl group are optionally substituted by 1 to 3 substituents each independently selected from a halogen atom, a haloalkyl group, an alkyl group, —(CH$_2$)$_h$—OH, —N(R$^{12}$)(R$^{13}$), —CN, —NO$_2$, an alkoxy group, a cycloalkyl group, an alkenyl group, —CO—R$^{14}$, an aryl group and a heteroaryl group, and the Y$_2$ ring is spiro cycloalkyl or spiro heterocycloalkyl ring, and $R^{27}$ and $R^{28}$ are each independently a hydrogen atom, a halogen atom, a haloalkyl group, an alkyl group, —(CH$_2$)$_h$—OH, —N(R$^{12}$)(R$^{13}$), —CN, —NO$_2$, an alkoxy group, a cycloalkyl group, an alkenyl group, —CO—R$^{14}$, an aryl group or a heteroaryl group;

Ar$^2$ is pyridyl;

and the pyrazole ring labeled A, is selected from

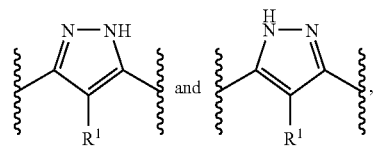

a prodrug thereof or a pharmaceutically acceptable salt thereof.

2. The pyrazole compound of claim 1, where m is 0, a prodrug thereof or a pharmaceutically acceptable salt thereof.

3. The pyrazole compound of claim 2, where Ar$^1$ is a phenyl group.

4. The pyrazole compound of claim 3, where R$^6$ and R$^7$ are each independently a halogen atom or a hydrogen atom.

5. A pharmaceutical composition comprising the pyrazole compound of claim 1, a prodrug thereof or a pharmaceutically acceptable salt thereof, and a pharmaceutically acceptable carrier.

* * * * *